(12) United States Patent
Arranz

(10) Patent No.: US 8,293,700 B2
(45) Date of Patent: Oct. 23, 2012

(54) ANTI-BACTERIAL COMPOSITION ESPECIALLY FOR CONTROLLING GRAM-NEGATIVE BACTERIA, COMPRISING A PEPTIDE AND AN ADVANTAGEOUSLY HYDROPHOBIC ANTI-BACTERIAL AGENT

(75) Inventor: Valérie Arranz, Monthyon (FR)

(73) Assignee: Cellectis, Romainville (FR)

( * ) Notice: Subject to any disclaimer, the term of this patent is extended or adjusted under 35 U.S.C. 154(b) by 824 days.

(21) Appl. No.: 10/568,104

(22) PCT Filed: Aug. 13, 2004

(86) PCT No.: PCT/FR2004/002142
§ 371 (c)(1),
(2), (4) Date: Mar. 19, 2007

(87) PCT Pub. No.: WO2005/018650
PCT Pub. Date: Mar. 3, 2005

(65) Prior Publication Data
US 2007/0259813 A1     Nov. 8, 2007

(30) Foreign Application Priority Data

Aug. 14, 2003  (EP) .................................... 03292030
Aug. 14, 2003  (FR) .................................... 03 09962

(51) Int. Cl.
*A61K 38/00*     (2006.01)
*C07K 16/00*    (2006.01)
*C07K 1/00*      (2006.01)

(52) U.S. Cl. ....... 514/1.1; 530/391.7; 530/326; 530/402

(58) Field of Classification Search .......................... None
See application file for complete search history.

(56) References Cited

U.S. PATENT DOCUMENTS

| | | |
|---|---|---|
| 3,710,795 A | 1/1973 | Higuchi et al. |
| 4,526,888 A | 7/1985 | Hottendorf et al. |
| 5,262,564 A | 11/1993 | Kun et al. |
| 5,521,291 A | 5/1996 | Curiel et al. |
| 5,547,929 A | 8/1996 | Anderson et al. |
| 5,624,894 A | 4/1997 | Bodor |
| 5,635,383 A | 6/1997 | Wu et al. |
| 6,043,339 A | 3/2000 | Lin et al. |
| 6,066,485 A | 5/2000 | Guthridge et al. |
| 6,274,712 B1 | 8/2001 | Springer et al. |
| 6,750,321 B1 | 6/2004 | Chen et al. |
| 6,835,536 B2 | 12/2004 | Krieger et al. |
| 6,855,801 B1 | 2/2005 | San Antonio et al. |
| 7,049,286 B2 | 5/2006 | Tchelingerian |
| 7,112,562 B2 | 9/2006 | Tchelingerian |
| 2003/0153490 A1 | 8/2003 | Tchelingerian |
| 2003/0199677 A1 | 10/2003 | Avrameas et al. |
| 2004/0123343 A1 | 6/2004 | La Rosa et al. |
| 2006/0281897 A1 | 12/2006 | Trouet et al. |
| 2007/0042492 A1 | 2/2007 | Avrameas et al. |
| 2007/0259813 A1 | 11/2007 | Arranz |

FOREIGN PATENT DOCUMENTS

| | | |
|---|---|---|
| FR | 2 766 826 | 5/1999 |
| WO | WO 90/12587 | 11/1990 |
| WO | WO 91/04315 | 4/1991 |
| WO | WO 94/28921 | 12/1994 |
| WO | WO 96/06632 | 3/1996 |
| WO | WO 96/08274 | 3/1996 |
| WO | WO 96/38163 | 12/1996 |
| WO | WO 97/02840 | 1/1997 |
| WO | WO 98/40401 | 9/1998 |
| WO | WO 98/56938 | 12/1998 |
| WO | WO 99/06632 | 2/1999 |
| WO | WO 99/07414 | 2/1999 |
| WO | WO 99/32136 | 7/1999 |
| WO | WO 99/67284 | 12/1999 |
| WO | WO 00/45831 | 8/2000 |
| WO | WO 01/64738 | 9/2001 |
| WO | WO 03/018636 | 3/2003 |
| WO | WO 03/092736 | 11/2003 |
| WO | WO 03/106491 | 12/2003 |
| WO | WO 2004/011033 | 2/2004 |
| WO | WO 2005/016960 | 2/2005 |
| WO | WO2005/016960 A2 | 2/2005 |

OTHER PUBLICATIONS

Darveau, et al. (1991) "β-lactam Antibiotics Potentiate Magainin 2 Antimicrobial Activity in vitro and in vivo" *Antimicrobial Agents and Chemotherapy* 35(6): 1153-1159.
Park, et al. (1998) *Biochem. Biophys. Res. Commun.* 244(1): 253-257.
Accession No. 600165A (Jul. 10, 1992) Insulin.
Accession No. 550085A (Jul. 10, 1992) Insulin.
Accession No. AAH05255 (Jun. 23, 2006) Insulin [*Homo sapiens*].
Accession No. AAA59179 (Jan. 6, 1995) Insulin [*Homo sapiens*].
Accession No. AAW99570 (Feb. 14, 2005) Sequence 35 from U.S. Patent No. 6,835,536.
Amara, et al. (1999) Journal of Biological Chemistry 274: 23916-23925.
Arkonac, et al. (1998) Journal of Biological Chemistry 273: 4400-4405.
Avrameas, et al. (1998) Proc. Natl. Acad. Sci. 95: 5601-5606.
Avrameas, et al. (1999) Bioconjugate Chemistry 10(1) : 87-93.
Bernfield, et al. (1992) Annu. Rev. Cell Biol. 8: 365-393.

(Continued)

*Primary Examiner* — S. Devi
(74) *Attorney, Agent, or Firm* — Arent Fox LLP

(57) ABSTRACT

The invention relates to an anti-bacterial composition, especially for controlling gram-negative bacteria, containing a combination of: a) at least one peptide of between 10 and 25 amino acid residues comprising: i) two positively charged domains with a neutral pH consisting of between 3 and 9 amino acid residues, at least two thirds thereof being cationic amino acids, ii) a group of two to three non-cationic amino acid residues located between said positively charged domains, iii) a group of between 0 and 10, preferably between 0 and 5, amino acid residues selected from the group comprising non-hydrophobic amino acids and positively charged amino acids, located at one of the terminal ends N or C of the peptide, a positively charged amino acid residue, however, not being directly adjacent to the positively charged domains; and b) at least one anti-bacterial compound.

3 Claims, 4 Drawing Sheets

OTHER PUBLICATIONS

Bosanquet (1986) Cancer Chemother. Pharmacol. 18: 176-179.
Caldwell, et al. (1996) Int. J. Biochem. Cell Biol. 28: 203-216.
Campanelli, et al. (1996) Development 122: 1663-1672.
Cardin & Weintraub (1989) Artheriosclerosis 9: 21-32.
Cardin, et al. (1988) Biochem. Biophys. Res. Corn. 154: 741-745.
Castellot, et al. (May 1986) J. Cell Biol. 102: 1979-1984.
David (1993) FASEB J. 7: 1023-1030.
Dini, et al. (1996) Cellular and Molécular Biology 42(2): 269-277.
Esko, et al. (1985) Proc. Natl. Acad. Sci. 82: 3197-3201.
Fowlkes, et al. (1997) Endocrinol 138: 2280-2285.
Fromm, et al. (1997) Arch. Biochem. Biophys. 343(1): 92-100.
Grieb, et al. (1998) Biochem. Biophys. Res. Comm. 246: 182-191.
Gueritte-Voegelein (1991) J. Med. Chem. 34: 992-998.
Guevara, et al. (1999) Journal of Protein Chemistry 18(8): 845-857.
Hasan, et al. (1999) J. Immunol. 162: 1064-1070.
Hirabayashi, et al. (1993) Scand. J. Immunol. 37: 533-540.
Hirsch (1991) New Engl. J. Med. 324: 1565-1574.
Inoue, et al. (1990) FEBS 269: 89-92.
Javadpour, et al. (1996) J. Med. Chem. 39: 3107-3113.
Kallunski & Tryggvason (Jan. 1992) The Journal of Cell Biology 116(2): 559-571.
Kalsi, et al. (1995) Lupus 4: 375-389.
Lookene, et al. (2000) Biochemistry 39: 230-236.
Lortat-Jacob & Grimaud (1991) FEBS 280: 152-154.
Maher, et al. (1989) Mol. Cell Biol. 9: 2251-2253.
Margalit, et al. (1993) Journal of Biological Chemistry 265(26): 19228-19231.
Mesri, et al. (1994) Journal of Cell Science 107 : 2599-2608.
Morrow (1991) J. Biol. Chem. 273(32): 20114-20120.
Ngo, et al. (1995) *The Protein Folding Problem and Tertiary Structure Prediction* pp. 491-495.
Niidome, et al. (1999) Bioconjugate Chemistry 10(5): 773-780.
Nogales (1999) Cell. Mol. Life Sci. 56: 133-142.
Ohta, et al. (Apr. 1994) Free Radical Biology & Medicine 16(4): 501-507.
Olofsson, et al. (1999) Journal of Clinical Investigation 4: 885-894.
Pasqualini, et al. (1997) Nature Biotech. 15: 542-546.
Pohl, et al. (1990) FEBS 272: 200-204.
Robinson (1963) Adv. Lip. Res. 1:1 133-182.
Rostand and Esko (Jan. 1997) Infection and Immunity 65(1): 1-8.
Ruoslahti & Yamazuchi (Mar. 1991) Cell 64: 867-869.
Salmivira & Jalkanen (1995) Experentia 51: 863-872.
Silber, et al. (Nov. 15, 1994) Blood 84(10): 3440-3446.
Stevenson, et al. (1993) J. Autoimmunity 6: 809-825.
Stoll, et al. Journal of Controlled Release 64: 217-218 (2000).
Tabosa Do Egito, et al. (Sep. 1996) J. Antimicrob. Vhemother. 38(3): 485-497.
Ternynck, et al. (1987) "Techniques immunoenzymatiques" Editions INSERM.
Travis J. (Oct. 5, 1994) Journal of the National Cancer Institute 86(19): 1450-1457.
Wall and Wani (Feb. 15, 1995) Cancer Research 55: 753-760.
Weisgraber and Rall (1987) Journal of Biological Chemistry 262(23): 11097-11103.
Xu, et al. (1996) Glycoconjugate Journal 13: 81-90.
Yayon, et al. (Feb. 22, 1991) Cell 64: 841-848.
Zunino, et al. (1999) Drug Resistance Updates 2: 351-357.
Requirement for Restriction/Election of Nov. 10, 2005 from U.S. Appl. No. 10/231,889.
Non-Final Rejection of Jun. 27, 2006 from U.S. Appl. No. 10/231,889.
Final Rejection of Apr. 5, 2007 from U.S. Appl. No. 10/231,889.
Non-Final Rejection of Jan. 9, 2008 from U.S. Appl. No. 10/231,889.
Final Rejection of Aug. 5, 2008 from U.S. Appl. No. 10/231,889.
Requirement for Restriction/Election of Apr. 18, 2007 from U.S. Appl. No. 10/568,108.
Non-Final Rejection of Jul. 23, 2007 from U.S. Appl. No. 10/568,108.
Final Rejection of Dec. 11, 2007 from U.S. Appl. No. 10/568,108.
Notice of Allowance and Fees Due of May 30, 2008 from U.S. Appl. No. 10/568,108.

SEQUENCE LISTING

<160> NUMBER OF SEQ ID NOS: 23

<210> SEQ ID NO 1
<211> LENGTH: 16
<212> TYPE: PRT
<213> ORGANISM: Homo sapiens

<400> SEQUENCE: 1

Arg Lys Lys Arg Arg Arg Glu Ser Arg Lys Lys Arg Arg Arg Glu Ser
1               5                   10                  15

<210> SEQ ID NO 2
<211> LENGTH: 18
<212> TYPE: PRT
<213> ORGANISM: Homo sapiens

<400> SEQUENCE: 2

Arg Lys Lys Arg Arg Arg Glu Ser Arg Arg Ala Arg Arg Ser Pro Arg
1               5                   10                  15

His Leu

<210> SEQ ID NO 3
<211> LENGTH: 17
<212> TYPE: PRT
<213> ORGANISM: Homo sapiens

<400> SEQUENCE: 3

Gly Arg Pro Arg Glu Ser Gly Lys Lys Arg Lys Arg Lys Arg Leu Lys
1               5                   10                  15

Pro

```
<210> SEQ ID NO 4
<211> LENGTH: 15
<212> TYPE: PRT
<213> ORGANISM: Homo sapiens

<400> SEQUENCE: 4

Gly Lys Arg Lys Lys Gly Lys Leu Gly Lys Lys Arg Asp Pro
1               5                   10                  15

<210> SEQ ID NO 5
<211> LENGTH: 17
<212> TYPE: PRT
<213> ORGANISM: Homo sapiens

<400> SEQUENCE: 5

Gly Lys Arg Lys Lys Gly Lys Leu Gly Lys Lys Arg Pro Arg Ser
1               5                   10                  15

Arg

<210> SEQ ID NO 6
<211> LENGTH: 16
<212> TYPE: PRT
<213> ORGANISM: Homo sapiens

<400> SEQUENCE: 6

Leu Arg Arg Glu Arg Gln Ser Arg Leu Arg Arg Glu Arg Gln Ser Arg
1               5                   10                  15

<210> SEQ ID NO 7
<211> LENGTH: 22
<212> TYPE: PRT
<213> ORGANISM: Homo sapiens

<400> SEQUENCE: 7

Gly Ala Tyr Asp Leu Arg Arg Arg Glu Arg Gln Ser Arg Leu Arg Arg
1               5                   10                  15

Arg Glu Arg Gln Ser Arg
            20

<210> SEQ ID NO 8
<211> LENGTH: 19
<212> TYPE: PRT
<213> ORGANISM: Homo sapiens

<400> SEQUENCE: 8

Val Lys Arg Gly Leu Lys Leu Arg His Val Arg Pro Arg Val Thr Arg
1               5                   10                  15

Met Asp Val

<210> SEQ ID NO 9
<211> LENGTH: 10
<212> TYPE: PRT
<213> ORGANISM: Homo sapiens

<400> SEQUENCE: 9

Ala Lys Thr Gly Lys Arg Lys Arg Ser Gly
1               5                   10

<210> SEQ ID NO 10
<211> LENGTH: 13
<212> TYPE: PRT
<213> ORGANISM: Homo sapiens

<400> SEQUENCE: 10
```

Gln Gly Lys Ser Lys Arg Glu Lys Lys Asp Arg Val Phe
1               5                   10

<210> SEQ ID NO 11
<211> LENGTH: 18
<212> TYPE: PRT
<213> ORGANISM: Homo sapiens

<400> SEQUENCE: 11

Val Lys Arg Gly Leu Lys Leu Arg Gln Lys Tyr Asn Lys Arg Ala Met
1               5                   10                  15

Asp Tyr

<210> SEQ ID NO 12
<211> LENGTH: 22
<212> TYPE: PRT
<213> ORGANISM: Homo sapiens

<400> SEQUENCE: 12

Asn Pro Gly Val Ser Thr Val Val Leu Gly Ala Tyr Asp Leu Arg Arg
1               5                   10                  15

Arg Glu Arg Gln Ser Arg
            20

<210> SEQ ID NO 13
<211> LENGTH: 6
<212> TYPE: PRT
<213> ORGANISM: Homo sapiens

<400> SEQUENCE: 13

Arg Lys Lys Arg Arg Arg
1               5

<210> SEQ ID NO 14
<211> LENGTH: 3
<212> TYPE: PRT
<213> ORGANISM: Homo sapiens

<400> SEQUENCE: 14

Arg Pro Arg
1

<210> SEQ ID NO 15
<211> LENGTH: 7
<212> TYPE: PRT
<213> ORGANISM: Homo sapiens

<400> SEQUENCE: 15

Lys Arg Lys Lys Lys Gly Lys
1               5

<210> SEQ ID NO 16
<211> LENGTH: 4
<212> TYPE: PRT
<213> ORGANISM: Homo sapiens

<400> SEQUENCE: 16

Arg Arg Glu Arg
1

<210> SEQ ID NO 17
<211> LENGTH: 5
<212> TYPE: PRT
<213> ORGANISM: Homo sapiens

```
<400> SEQUENCE: 17

Arg Arg Arg Glu Arg
1               5

<210> SEQ ID NO 18
<211> LENGTH: 8
<212> TYPE: PRT
<213> ORGANISM: Homo sapiens

<400> SEQUENCE: 18

Arg Arg Ala Arg Arg Ser Pro Arg
1               5

<210> SEQ ID NO 19
<211> LENGTH: 9
<212> TYPE: PRT
<213> ORGANISM: Homo sapiens

<400> SEQUENCE: 19

Lys Lys Arg Lys Arg Lys Arg Leu Lys
1               5

<210> SEQ ID NO 20
<211> LENGTH: 3
<212> TYPE: PRT
<213> ORGANISM: Homo sapiens

<400> SEQUENCE: 20

Lys Lys Arg
1

<210> SEQ ID NO 21
<211> LENGTH: 7
<212> TYPE: PRT
<213> ORGANISM: Homo sapiens

<400> SEQUENCE: 21

Lys Lys Arg Pro Arg Ser Arg
1               5

<210> SEQ ID NO 22
<211> LENGTH: 6
<212> TYPE: PRT
<213> ORGANISM: Homo sapiens

<400> SEQUENCE: 22

Arg Leu Arg Arg Glu Arg
1               5

<210> SEQ ID NO 23
<211> LENGTH: 7
<212> TYPE: PRT
<213> ORGANISM: Homo sapiens

<400> SEQUENCE: 23

Arg Leu Arg Arg Arg Glu Arg
1               5
```

ANTI-BACTERIAL COMPOSITION ESPECIALLY FOR CONTROLLING GRAM-NEGATIVE BACTERIA, COMPRISING A PEPTIDE AND AN ADVANTAGEOUSLY HYDROPHOBIC ANTI-BACTERIAL AGENT

CROSS-REFERENCE TO RELATED APPLICATIONS

This application is the National Stage Application of International Application No. PCT/FR2004/002142, filed Aug. 13, 2004, which claims the benefit of French Patent Application No. 0309962, filed Aug. 14, 2003 and European Patent Application No. 03292030.8, filed Aug. 14, 2003, the disclosures of each of which are herein incorporated by reference in their entireties.

BACKGROUND OF THE INVENTION

1. Field of the Invention

The present invention relates to the field of antibacterial therapy, and more specifically, methods and compositions for treating infections caused by Gram-negative bacteria in humans, animals and plants.

2. Description of the Related Art

Peptides with the ability to destroy bacteria are described in the prior art (C B Park, H S Kim, S C Kim. Biochem Biophys Res Commun. Mar. 6, 1998; 244(1): 253-7). Likewise, peptides capable of reacting with aminoglycans and transporting molecules of interest in eukaryotic or prokaryotic cells are disclosed in international patent application PCT No. WO 01/64738.

The amount of antibiotic molecules penetrating the bacterium depends on their structure and the mechanisms involved in transporting substrates. Gram-negative bacteria differ structurally from Gram-positive bacteria due the presence of two membranes that constitute the bacterial envelope. If all the bacteria have an internal membrane, then Gram-negative bacteria have an additional single external membrane. This external hydrophobic membrane forms a semi-permeable, barrier preventing antibiotics from penetrating, while porines, i.e., proteins forming channels, allow small hydrophilic solutes, such as nutritional elements and antibiotics of the penicillin and tetracycline family to enter, while preventing the penetration of large molecules and antibiotics of the macrolides/ketolides family.

An important reason for therapeutic failures to control the Gram-negative bacteria is the emergence of resistant strains. Certain resistances are related to a reduction of the permeability of bacterial membranes (quantitative/qualitative modifications of porines). Other resistances are due to the presence of a membranous protein causing the rejection of the antibiotic through an active efflux mechanism. The development of new types of antibacterial molecules or the application of non-active commercial antibiotics on the Gram-negative bacteria requires their entrance and delivery across selective bacterial membranes.

The object of the present invention is precisely to provide new methods and compositions that allow for effective treatment of infections caused by Gram-negative bacteria, even when these have developed resistance to antibiotics.

This object is obtained by using peptides capable of passing through the external membrane of Gram-negative bacteria, and through this membranal translocation, deliver molecules of interest that otherwise would not penetrate into the interior of bacteria, because of their physiochemical properties.

Penetration into the interior of the bacteria means that the peptides of the invention facilitate or allow the penetration of the molecules of interest into bacteria. The terms penetration and internalization are henceforth used synonymously.

The work performed in connection with the present invention concerned Bodipy and tetramethylrhodamine that are hydrophobic fluorescent molecules excluded by the external membrane of the Gram-negative bacteria. These fluorescent tracers were chosen in order to evaluate the internalization properties of the peptides of the invention being chemically bound to hydrophobic molecules. The translocation of fluorescent tracers in the Gram-negative bacterium was evaluated qualitatively on *Escherichia coli* and *Pseudomonas aeruginosa*.

BRIEF SUMMARY OF THE INVENTION

Thus, the object of the present invention is primarily an antibacterial composition, more particularly in order to control the Gram-negative bacteria, comprising an association:

a) of at least one peptide of 10-25 amino-acid residues comprising:

i) two positively charged domains at neutral pH, each consisting of 3-9 amino-acid residues, of which at least two-thirds are cationic amino acids, ii) between the said positively charged domains, a group of two or three non-cationic amino-acid residues, iii) at either N- or C-terminal extremity of the peptide, a group of 0-10, preferably 0-5, amino-acid residues chosen from the group comprising non-hydrophobic amino acids and positively charged amino acids, however, in case of a positively charged amino acid residue, the latter is not immediately adjacent to the positively charged domains.

b) at least one anti-bacterial compound.

DETAILED DESCRIPTION OF THE INVENTION

Figure 1:
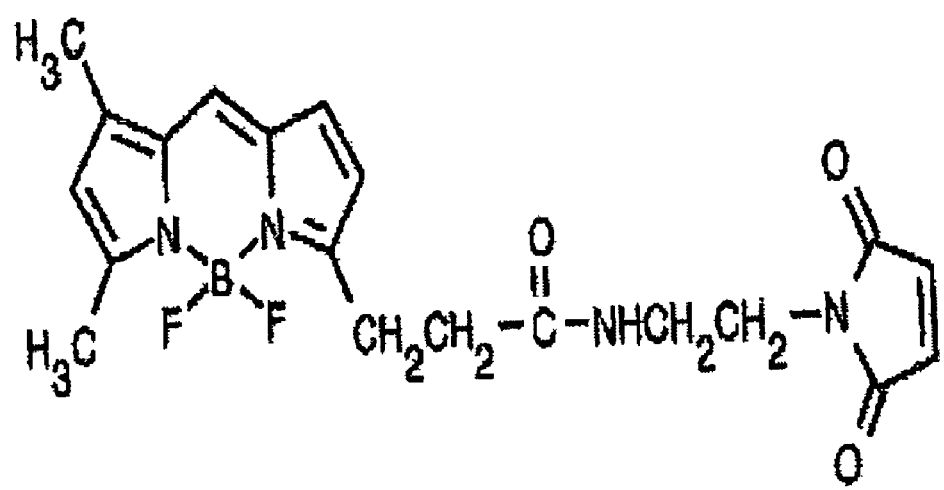
FIG. 1 represents the formula of Bodipy® FL N-(2-aminoethyl) maleimide.

The peptides of the invention are thus especially suitable for the preparation of a pharmaceutical composition intended to treat an infection, more specifically by Gram-negative bacteria, and in which composition the said peptide passes through the bacterial membrane in order to deliver to the interior of the bacteria an antibacterial compound to which it is associated in the said composition.

In the peptides of the above-mentioned invention, the cationic amino acids of the two positively charged domains are advantageously chosen from the group comprising arginine and lysine.

In the peptides of the above-mentioned invention, the non-cationic amino acids of the group between the said positively charged domains are preferably amino acids:
- that are non-hydrophobic and chosen, e.g., from the group comprising glutamic acid, serine, glycine, and glutamine, or
- leucine (hydrophobic amino acid).

The orientation of the amino-acid sequence according to the invention is typically N-terminal toward C-terminal. However, according to another embodiment, the orientation may be reversed, whereby the amino-acid sequences are oriented from the C-terminal toward the N-terminal.

Preferred peptides for the compositions according to the invention are chosen from the group comprising the following sequences (N-terminal toward C-terminal orientation):

DPV3:
```
Arg Lys Lys Arg Arg Arg Glu Ser Arg Lys Lys Arg      (SEQ ID.NO: 1)
Arg Arg Glu Ser
```

DPV3.10:
```
Arg Lys Lys Arg Arg Arg Glu Ser Arg Arg Ala Arg      (SEQ ID.NO: 2)
Arg Ser Pro Arg His Leu
```

DPV6:
```
Gly Arg Pro Arg Glu Ser Gly Lys Lys Arg Lys Arg      (SEQ ID.NO: 3)
Lys Arg Leu Lys Pro
```

DPV7:
```
Gly Lys Arg Lys Lys Lys Gly Lys Leu Gly Lys Lys      (SEQ ID.NO: 4)
Arg Asp Pro
```

DPV7b:
```
Gly Lys Arg Lys Lys Lys Gly Lys Leu Gly Lys Lys      (SEQ ID.NO: 5)
Arg Pro Arg Ser Arg
```

DPV15:
```
Leu Arg Arg Glu Arg Gln Ser Arg Leu Arg Arg Glu      (SEQ ID.NO: 6)
Arg Gln Ser Arg
```

DPV15b:
```
Gly Ala Tyr Asp Leu Arg Arg Arg Glu Arg Gln Ser      (SEQ ID NO. 7)
Arg Leu Arg Arg Glu Arg Gln Ser Arg
```

DPV1047:
```
Val Lys Arg Gly Leu Lys Leu Arg His Val Arg Pro      (SEQ ID NO. 8)
Arg Val Thr Arg Met Asp Val
```

DPV11:
```
Ala Lys Thr Gly Lys Arg Lys Arg Ser Gly             (SEQ ID.NO: 9)
```

DPV1121:
```
Val Lys Arg Gly Leu Lys Leu Arg Gln Lys Tyr Asn     (SEQ ID.NO: 11)
Lys Arg Ala Met Asp Tyr
```

Among these, the invention relates most especially to the following peptides: DPV3, DPV3.10, DPV6, DPV7, DPV7b, DPV15 and DPV15b.

The alignment of the above sequences highlights positively charged domains of the following sequences:

```
Arg Lys Lys Arg Arg Arg                    (SEQ ID.NO: 13)
Arg Pro Arg                                (SEQ ID.NO: 14)
Lys Arg Lys Lys Lys Gly Lys                (SEQ ID.NO: 15)
30 Arg Arg Glu Arg                         (SEQ ID.NO: 16)
Arg Arg Arg Glu Arg                        (SEQ ID.NO: 17)
Arg Arg Ala Arg Arg Ser Pro Arg            (SEQ ID NO. 18)
Lys Lys Arg Lys Arg Lys Arg Leu Lys        (SEQ ID.NO: 19)
Lys Lys Arg                                (SEQ ID.NO: 20)
Lys Lys Arg Pro Arg Ser Arg                (SEQ ID.NO: 21)
Arg Leu Arg Arg Glu Arg                    (SEQ ID.NO: 22)
Arg Leu Arg Arg Arg Glu Arg                (SEQ ID.NO: 23)
```

The domains of the sequences SEQ. ID. NO:13-17 are preferably adjacent to the N-terminal extremity of the peptide, while the domains of the sequences SEQ ID. NO:18-23 are adjacent to the C-terminal extremity of the peptide.

The alignment of the above sequences also highlights groups of two or three non-cationic amino-acid residues between the positively charged domains of the following sequences:
Glu Ser, Glu Ser Gly, Leu Gly, Gln Ser The anti-bacterial compounds present in the compositions according to the invention are preferably chosen from those that present physiochemical properties rendering them incapable of passing through a membrane of Gram-negative bacteria. Most preferably, this concerns hydrophobic antibacterial compounds. Among such compounds are antibiotics of the macrolides family, ketolides, such as erythromycin, clarithromycine, azithromycine, and telithromycine.

The anti-bacterial compounds may also be antisense oligonucleotides.

The evaluation of the DPV peptides above has shown their capacity to pass through membranes of the Gram-negative bacteria *E. coli* or *P. aeruginosa*, and deliver Bodipy in the bacterium, even though the former is a hydrophobic molecule that is normally excluded by the external membrane of Gram-negative bacteria representing a semi-permeable barrier. Moreover, it appears that these peptides are able to pass through the external membrane of the two Gram-negative bacterial strains and accumulate in the bacterial cytoplasm through a mechanism that is non-energy-dependent and non-toxic for the bacterium.

The work performed in connection with the invention has shown some internalization differences between the two strains of bacteria *P. aeruginosa* and *E. coli*. Thus, it appears that the DPV7b peptide is more internalizing in *P. aeruginosa* than in *E. coli*. This difference might be explained by the structural differences of the external membrane between the two-bacterial strains.

These peptides are hence useful for preparing antibacterial pharmaceutical compositions, more particularly against Gram-negative bacteria, where they are combined with one or more antibacterial agents.

The compositions of the invention are useful both for preventive and curative purposes.

Moreover, the compositions according to the invention advantageously comprise one or more vehicles, diluents or excipients that are pharmaceutically acceptable and generally used with this type of agents.

The peptides of the invention may be prepared by chemical synthesis or genetic engineering in a prokaryotic cell, such as a bacterium, a eukaryotic cell, such as a yeast cell, a CHO (Chinese Hamster Ovary) cell, an NSO (Mouse myeloma cells) cell, a transgenic animal, e.g., in the milk of a rabbit, a goat, a ewe, a cow, etc., or in a transgenic plant, e.g., tobacco plants, etc.

The invention also relates to functional equivalents of the peptides defined above, such as peptides comprising the modifications issuing from the post-translational process, such as glycosylation, or chemical modifications, such as coupling with lipids, sugars, nucleotide sequences, in case these modifications do not modify the anti-bacterial and/or anti-fungal activity of the said peptides in conformance with the tests provided in the experimental section below. The functional equivalents also comprise peptides in which one or more amino acids are D-conformation amino acids. The invention also covers retropeptides and retro-inverso peptides.

The association of compositions according to the invention may consist of one or more of the peptides described above and one or more antibacterial compounds, and unless otherwise stated, the singular form used in the definition of the active agents (peptide and anti-bacterial compound) shall also be construed as the plural.

The composition according to the invention may be realized by associating peptide(s) and anti-bacterial compound(s) in a mixture or a product, in which one or more identical or different peptides are covalently bound to one or more identical or different compounds, e.g., by means of a spacer arm. Such products are notably products of formula (I), which will be described in the following.

If administering the peptide and the anti-bacterial compound in a mixture, these two active agents of the anti-bacterial composition of the invention may be presented separately, each in an appropriate pharmaceutical form and combined in one packing. However, in order to facilitate simultaneous administration of the active agents, it is generally preferred to prepare the medication in one single pharmaceutical form containing the two active ingredients in a mixture, as well as perhaps a proper pharmaceutical excipient.

Naturally, a product consisting of a peptide bound directly or indirectly to an anti-bacterial compound should in itself be considered an association according to the invention and that may be used as a single active ingredient.

For instance, a peptide and an anti-bacterial compound may be combined by establishing a chemical bond between them. It is especially possible to amidify an amino function of the peptide, or esterify one or more alcohol functions of the peptide with an acid grouping that is present at the level of an anti-bacterial compound or a derivative thereof. Therefore, an amidification product forming the active product of the composition of the invention is obtained. It is also possible to add to either N- and/or C-terminal extremity of the peptide an amino-acid residue, whose lateral chain allows coupling with an anti-bacterial compound, such as a cysteine residue, whose SH group is reactive. Among such products are those of the formula (I) described below.

In fact, another object of the invention is to obtain new products, where the peptide and the anti-bacterial compound are covalently bound to one another, possibly by at least one spacer arm.

Such products are notably those corresponding to the following formula (I):

$$(A-)_m(X)_p(-P)_n \quad (I)$$

where A is the residue of an anti-bacterial compound, P is the residue of a peptide, as defined previously, and X represents either a covalent bond between A and P, or a spacer arm binding at least an A residue to at least one P residue, and m is an integer from 1 to 3, n is an integer from 1 to 3, and p represents zero or an integer at the most equal to the greater of the numbers m and n.

It is indeed possible to graft one or more A and/or P residues on one single spacer arm, or one or more A-X groups on a P residue (whereby m equals p and n equals 1), or one or more X—P groups on an A residue (whereby n equals p and m equals 1). When p equals zero, then either one or more A residues are bound directly to a P residue (and n equals 1), or one or more P residue are bound directly to an A residue (and m equals 1).

The products of formula (I) may be used in the form of salts, particularly in the form of alkaline metal salts, e.g., salts of sodium or potassium; these salts are, for example, those of the phosphate groupings, if present, the phenolic groupings (case of salicylic acid), etc. It is also possible to use products of formula (I), if need be, in the form of addition salts (e.g., in the form of hydrochlorate), when these products contain an amine grouping.

The bonds between the spacer arm and the A and P residues, or directly between A and P, are covalent bonds. These covalent bonds may be formed, as indicated previously, between carboxylic-ester, carboxylic-amide, thiocarboxylic-ester, or thiocarboxylic-amide groups.

The residues of the anti-bacterial compound (A) and the peptide (P) are derivatives of an antibacterial compound or peptide, whereby one or more chemical groups have been either suppressed or modified to allow for the formation of a covalent bond directly between A and P, or indirectly, by means of a spacer arm.

This may involve the acyle functions of antibacterial compounds possessing a carboxylic group capable of forming a bond with the spacer arm or the peptide, the latter possessing a primary amine or a hydroxyl group capable of forming a covalent bond with the spacer arm or the anti-bacterial compound.

The spacer arms may notably be bivalent residues of bifunctional aliphatic compounds, such as compounds with reactive functional groups at each of their extremities, allowing each to form covalent bonds with A and P. These compounds may, for example, be compounds with both an amino and a carboxylic (or thiocarboxylic) group, or compounds with both an amino group and a hydroxyl group.

In formula (I), the X group (disregarding its functional extremity groups) notably represents a divalent aliphatic group, possibly interrupted by one or more heteroatoms —O— or —S—, or one or more heteroatomic groups —NH— or —CO— —NH—.

Among the compounds capable of producing, after reaction with the peptide and the anti-bacterial compound or their derivatives, products of formula (I), in which A and P are bound by spacer arms, are alpha-, beta- or gamma-amino alcanecarboxylic acids, especially natural alpha-amino acids, such as glycine, alanine, valine or leucine, or peptides, specifically dipeptides or tripeptides. As indicated in the examples, this may advantageously involve a cysteine residue.

The spacer agents may likewise be hydroxy-carboxylic acids, such as lactic, glycolic, aldonic (gluconic, mannonic, galactonic, ribonic, arabinonic, xylonic and erythronic) acids and corresponding lactones or dilactones (e.g., lactide, glycolide, delta-glucolonactone, delta-valéronactone), or aldaric acids.

The functional groups perhaps present on the spacer arm and involved in the bond with A or P may be used in order to graft other A and/or P residues in order to obtain compounds of formula (I), for which m and/or n are greater than 1. This applies, for instance, to hydroxyl groups of hydroxyacids, the second carboxylic group of carboxylic amino-acid diacids, the second amino group of diamino amino acids, the hydroxyl group of hydroxylated amino acids, etc.

The spacer arm may advantageously consist of a binding molecule enabling delayed liberation of either or both of the A or P residues, notably by shielding them from degradation after administration. The spacer arm may also consist of a vectorization molecule allowing a particular organ or tissue to be targeted so as to deliver the residues of the anti-bacterial compound.

In order to prepare the compounds of formula (I), traditional methods of organic synthesis are used. For instance, to prepare amides or esters, it is possible to react a carboxylic compound in the form of a halide of carboxylic acid halide (or thiocarboxylic), in the form of a mixed anhydride, or in the form of an activated ester, e.g., a p-nitrophenylic ester. Activation of the acid by means of a coupling agent, such as dicyclohexylcarbodiimide, may also be done.

Since the compounds of formula (I) comprise peptide residues, their preparation may be done by using especially the methods known in peptide chemistry.

When the compounds, from which A, P or X of the formula (I) are derived, comprise several functions susceptible of reaction, it is naturally advisable to proceed by either using reagents in stoichiometric proportions (according to the number of precursor products of A and/or P preferably reacted), or temporarily protecting the reactive functions, if their reaction is not desired. Temporary protection methods of the said reactive functions are used for this These temporary reaction methods are well known, specifically those developed during peptide synthesis research. For example, the $-NH_2$ groups may be protected by carbobenzoxy, phtaloyl, t-butoxycarbonyl, trifluoroacetyl, toluenesulfonyl groups; the carboxylic groups may be protected in the form of benzylic esters, tetrahydropyranyl esters or t-butyl esters; alcohols may be protected in the form of esters (e.g., acetates), tetrahydropyranyl ethers, benzylic ethers or trityl ethers, or in the form of acetals (including in the form of acetonides in the case of vicinal glycols). Possible protection and deprotection reactions of various chemical groups are known and described in the literature.

The phosphation or dephosphation reactions of primary alcohol of nucleotides or nucleosides may be implemented by using natural enzymes (e.g., phosphatases, phosphokinases).

The antibacterial compositions of the invention, and particularly those comprising a compound of formula (I), may be administered by any of the modes of administration allowed by the therapeutic agents, i.e., oral, sublingual, nasal, pulmonary, rectal or parenteral (e.g., intravascular, intramuscular, transcutaneous, intra-articular). Systemic, topical or central administration, e.g., by the intracranial surgical route or even intra-ocular administration are also possible. Subcutaneous implantation of biodegradable implants may also be mentioned.

Hence, they may be presented in any form allowing for administration via:
oral route (especially in the form of capsules, solutions or emulsions to be taken orally, powders, gels, granules, pills or tablets), tablets, capsules, soft capsules, including formulations with delayed or prolonged release, pills, powders, granules, elixirs, tinctures, suspensions, syrups and emulsions. This presentation form is especially suited for the passage of the intestinal barrier and the most common use of antibacterial and/or antifungal compounds.
parenteral route, generally by intramuscular or intravenous injection by perfusion (drip). The injectable compositions may be prepared in the traditional way, either in a suspension or liquid solution or in solid form appropriate for extemporaneous dissolution in a proper liquid, including formulations for delayed or prolonged release, such as the inclusion of peptides in biodegradable micro- or nano-particles of lipid or dextran formulation, or PLGA or its equivalents. This presentation form is especially suitable for passage of the hemato-encephalic barrier, and the use of antibacterial and/or antifungal compounds in hospitals.

One possible parenteral administration uses the implantation of a slow or prolonged release system ensuring constant maintenance of dose levels.

Another possibility consists in fixing by adsorption or otherwise the peptides of the invention on a support, such as a catheter, a prosthesis or biological glue.
nasal route (e.g., solutions to be administered in the form of drops or sprays),
pulmonary route (solutions in a pressurized bottle for aerosols),
rectal route (suppositories),
coetaneous route (e.g., creams, ointments or transdermal devices, so-called patches),
transmucous route, e.g., by sublingual route (solutions in a pressurized bottle, or tablets for oral disintegration).

These pharmaceutical forms are prepared in the usual way and may contain appropriate traditional excipients and vehicles.

Other common topical preparations include creams, ointments, lotions, gels and aerosol sprays. The latter are more especially suited for the treatment of bacterial and/or broncho-pulmonary fungal infections.

The compositions of the invention may also be used in the cosmetic domain, essentially for preventive purposes, and consist of creams, nail polish, hygienic products for the genital organs, toothpastes, oral-hygiene solutions, or included in micro-particles for slow diffusion, in the aqueous phase, included, for example, in diapers, cotton swabs (Q-tips), bandages (band-aids), makeup-remover pads, sanitary towels or animal litter.

Depending on the mode of administration, the compounds may be in solid, semi-solid or liquid form.

As for solid compositions, such as tablets, pills, powders or free granules or included in capsules, the association may be combined with:
diluents, e.g., lactose, dextrose, sucrose, mannitol, sorbitol, cellulose and/or glycine;
lubricants, e.g., silica, talcum, stearic acid, its magnesium or calcium salt and/or polyethyleneglycol;
binders, e.g., silicate of magnesium and aluminum, starch paste, gelatin, tragacanth, methylcellulose, sodium carboxymethylcellulose and/or poly-vinylpyrrolidone; and if needed,
disintegrators, e.g., starch, agar, alginic acid or its sodium salt, or effervescent mixtures; and/or absorbants, colorants, flavoring agents and sweeteners. The excipients may be, e.g., mannitol, lactose, starch, magnesium stearate, sodic saccharine, talc, cellulose, glucose, sucrose, magnesium carbonate and pharmaceutical-grade analogs.

As for semi-solid compositions, such as suppositories, the excipient may be, for example, a fat emulsion or suspension, or based on polyalkyleneglycol, such as polypropylene-glycol.

The liquid compositions, especially those that are injectable or to be included in a soft capsule, may be prepared, e.g., by dissolution, dispersion, etc., of the active ingredient in a pharmaceutically pure solvent, such as water, physiological serum, aqueous dextrose, glycerol, ethanol, an oil and its analogs.

The compositions according to the invention may also be administered through a release system of the liposome type, e.g., in the form of small unilaminar vesicles, large unilaminar vesicles and multilaminar vesicles. The liposomes may be formed from a variety of phospholipids, containing cholesterol, stearylamine or phosphatidylcholines. In one embodiment, a film with liquid constituents may be hydrated with an aqueous solution of the medication in order to form a lipid layer encapsulating the medication.

The compositions according to the invention may be sterilized and/or contain adjuvants and non-toxic auxiliary substances, such as conservation, stabilization, moistening or emulsification agents, agents promoting dissolution, salts adjusting the osmotic pressure, and/or buffers. Moreover, other substances of therapeutic interest may be contained. The compositions are prepared by traditional mixing, granulation or coating methods, respectively, and contain about 0.1 to 75 percent, preferably about 1 to 50 percent, of the active ingredient The peptides and antibacterial agents of the association of the composition according to the invention may also be coupled to soluble polymers such as targetable medication supports. Such polymers may comprise polyvinylpyrrolidone, pyran copolymer, polyhydroxypropyl-methacrylamide-phenol, polyhydroxy-ethyl-aspanamide-phenol or poly (oxide of ethylene)-polylysine substituted by palmitoyl residues, dextran. Moreover, the compounds according to the present invention may be coupled to a class of biodegradable polymers that are useful for implementing controlled release of a medication, e.g., poly(lactic acid), poly(epsilon-caprolactone), poly(hydroxybutyric acid), polyorthoesters, polyacetals, polydihydropyrane, polycyanoacrylates and copolymers of reticulated or amphipatic-hydrogel sequences.

The dosage for administering compositions according to the invention is chosen based on many factors, including type, species, age, weight, sex and medical condition of the subject, the gravity of the condition to be treated, the administration route; the condition of the renal and hepatic functions of the subject, and the nature of the specific compound, or salt, employed. An average experienced physician or veterinarian will easily be able to determine and prescribe an efficient amount in order to prevent, impede or halt the progress of the medical condition to be treated.

A composition according to the invention may contain 0.1 to 99 percent, preferably 1 to 70 percent, of the active ingredient.

As examples, the oral dosages of the compositions according to the invention will be about 0.5 to 1 mg/day through oral ingestion, and preferably provided in the form of tablets containing 0.5, 1, 2.5, 5, 10, 15, 25, 50, 100, 250, 500 and 1,000 mg of the active ingredient. The efficient plasmatic concentrations will be obtained based on a dosage from 0.002 mg to 50 mg per kg of body weight and day.

The compositions of the invention may be administered in the form of single daily doses, or two, three or four daily doses.

EXAMPLES

Other advantages and characteristics of the invention appear from the examples in the following that are provided for illustration purpose, and which reference will be made to the Figures.

I—Materials and Methods

I.1) Fluorescent Tracers.

The Bodipy®FLN—(2-aminoethyl)maleimide (Bodipy) (Molecular Probes Cat #B-10250), whose molecular formula is $C_{20}H_{21}BF_2N_4O_3$, its molecular weight being 414.22 Da, the absorbance 504 nm and the emission 510 nm (green fluorescence), and the developed formula is shown in FIG. 1.

Figure 2:
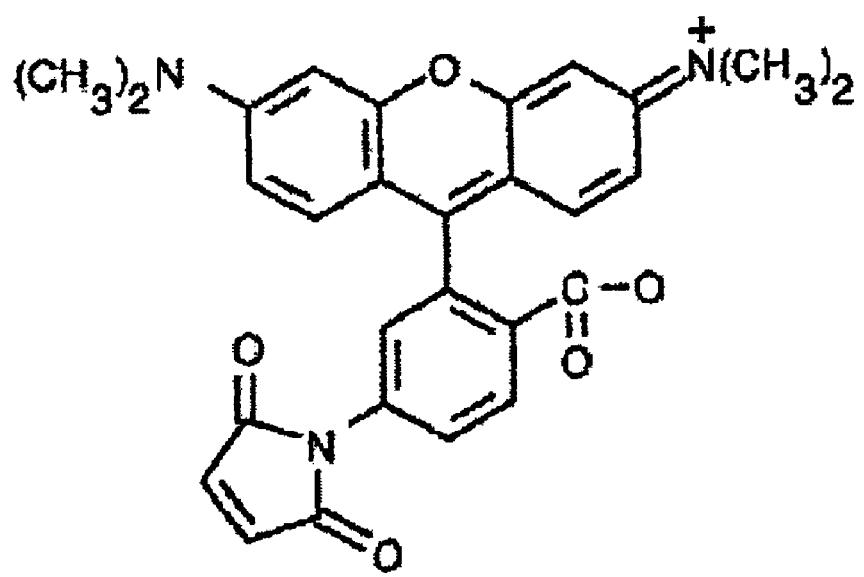
FIG. 2 represents the formula of tetramethylrhodamine-6-maleimide.

Tetramethylrhodamine-6-maleimide (TMR) (Molecular Probes Cat #T-6028), whose molecular formula is $C_{28}H_{23}NO_5$, its molecular weight being 481.51 Da, its absorbance 541 nm, its emission 567 nm (red fluorescence), and the developed formula is shown in FIG. 2.

These two fluorescent molecules contain a reactive maleimide group allowing chemical coupling on the thiol function of the cysteine of the peptide.

I.2) The Peptide Vectors (DPVs).

Peptides of the below sequences were used:

```
DPV3:
                                            (SEQ ID.NO: 1)
Arg Lys Lys Arg Arg Arg Glu Ser Arg Lys Lys Arg

Arg Arg Glu Ser
with a Cys (Cysteine) residue at its C-terminal
extremity,

DPV3.10:
                                            (SEQ ID.NO: 2)
Arg Lys Lys Arg Arg Arg Glu Ser Arg Arg Ala Arg

Arg Ser Pro Arg His Leu
with a Cys residue at its C-terminal extremity,

DPV6:
                                            (SEQ ID.NO: 3)
Gly Arg Pro Arg Glu Ser Gly Lys Lys Arg Lys Arg

Lys Arg Leu Lys Pro
with a Cys residue at its C-terminal extremity,

DPV7:
                                            (SEQ ID.NO: 4)
Gly Lys Arg Lys Lys Lys Gly Lys Leu Gly Lys Lys

Arg Asp Pro
with a Cys residue at its C-terminal extremity,

DPV7b:
                                            (SEQ ID.NO: 5)
Gly Lys Arg Lys Lys Lys Gly Lys Leu Gly Lys Lys

Arg Pro Arg Ser Arg
with a Cys residue at its C-terminal extremity,

DPV15:
                                            (SEQ ID.NO: 6)
Leu Arg Arg Glu Arg Gln Ser Arg Leu Arg Arg Glu

Arg Gln Ser Arg
with a Cys residue at its C-terminal extremity,

DPV15b:
                                            (SEQ ID.NO: 7)
Gly Ala Tyr Asp Leu Arg Arg Arg Glu Arg Gln Ser

Arg Leu Arg Arg Arg Glu Arg Gln Ser Arg
with a Cys residue at its N-terminal extremity,
```

```
DPV1047:
                                            (SEQ ID NO: 8)
Val Lys Arg Gly Leu Lys Leu Arg His Val Arg Pro

Arg Val Thr Arg Met Asp Val
with a Cys residue at its N-terminal extremity,

DPV11:
                                            (SEQ ID.NO: 9)
Ala Lys Thr Gly Lys Arg Lys Arg Ser Gly
with a Cys residue at its C-terminal extremity, DPV12:
                                           (SEQ ID.NO: 10)
Gin Gly Lys Ser Lys Arg Glu Lys Lys Asp Arg Val Phe
with a Cys Cys at its C-terminal extremity, DPV1121:
                                           (SEQ ID.NO: 11)
Val Lys Arg Gly Leu Lys Leu Arg Gin Lys Tyr Asn Lys Arg Ala Met Asp Tyr
with a Cys residue Cys at its N-terminal
extremity, DPV19:
                                           (SEQ ID.NO: 12)
Asn Pro Gly Val Ser Thr Val Val Leu Gly Ala Tyr Asp Leu Arg Arg Arg Glu Arg Gin Ser Arg
with a Cys residue at its N-terminal extremity.
```

The peptide syntheses were implemented according to methods known to a person skilled in the art. The peptides are soluble in water.

The peptides have a cysteine in the N- or C-terminal position to allow for the conjugation at the fluorescent tracer.

1.3) The Control Products.

Bodipy and TMR are chemically coupled to a cysteine residue and act as a negative indicator of internalization.

1.4) Chemical Coupling Method.

The Bodipy or TMR solutions were prepared at a final, concentration of 50 mM in 30 dimethylformamide (DMF). The DVP solutions were prepared at a final concentration of 10 mM in DMF. 200 μl of the Bodipy or TMR solution were mixed at 700 μl of the DPV solution. After incubation for 2 hours at ambient temperature and in darkness, 2 ml of $H_2O$ and 8 ml of dichloromethane (DCM) were added. The solution was vortex-mixed and centrifuged for 2 minutes at 3000 G. The aqueous phase was removed and stored. Four consecutive DCM extractions were made. The aqueous phases were collected in a glass bottle and allowed to stand for one hour at −80° C., before being freeze-dried for a minimum of 18 hours. The obtained powder was stored under argon at −20° C. away from light.

1.5) Conservation of the Conjugates in Solution.

The DPV-Bodipy and DPV-TMR conjugates were preserved diluted to 3 mM in $H_2O$ at −20° C., away from light.

1.6) HPLC Analysis of the Conjugates.

For the Bodipy conjugates:

Luna column of 100 Å 3μ C18 100×4.6 mm

Solvent A: 0.1% TFA in $H_2O$

Solvent B: 0.1% TFA in acetonitrile (CAN)

Gradient: 5% B to 60% in 10 mins., 60% B to 90% 20 in 1 min., 90% B for 3 mins., 5% B for 2 mins.

Flux: 1.2 ml/min; injected volume: 10 μl; the concentration of the injected sample was 1 mg/ml in 0.1% TFA Detector: DAD: 214 nm, 300 nm.

For the TMR conjugates:

Luna column of 100 Å3μ C18 100×4.6 mm

Solvent A: 0.1% TFA in $H_2O$

Solvent B: 0.1% TFA in acetonitrile (CAN)

Gradient: 5% B to 60% in 10 mins., 60% B in 90% in 1 min., 90% B for 3 mins., 5% B for 2 mins.

Flux: 1.2 ml/min; injected volume: 20 μl; the concentration of the injected sample was 1 mg/ml in 0.1% TFA Detector: DAD: 22 0 nm.

1.7) Bacterial Strains.

*Escherichia coli* ATCC 25922

*Pseudomonas aeruginosa* ATCC. 27853

1.8) Internalization Protocol.

I.8.a) Evaluation of the Penetration of Conjugates in the Bacterium at 37° C.

The bacteria in an exponential phase of culture were centrifuged and washed three times with the 10 mM, pH7.4 sodium phosphate buffer (NAPB buffer). The bacterial concentration was adjusted to $1×10^6$ cfu/ml (colony-forming units) in the NAPB buffer. 50 μl of the bacterial suspension was deposited on a poly-L-Lysine slide. After 30 minutes incubation at 37° C. in a humid chamber, the bacteria immobilized on the slide were rinsed three times with the NAPB buffer. A 50 μl solution of DPV-Bodipy or DPV-TMR conjugate or control product was, deposited on the bacteria. After incubation for 30 minutes at 37° C. in a humidity chamber and away from light, the slides were rinsed three times with the NAPB buffer. The bacteria may be fixed on the slide by incubating 20 minutes at 37° C., away from light. A drop of 50% PBS/Glycerol was deposited on the slide and covered by a cover glass. After sealing the cover glass on the slide, bacterial fluorescence was observed under a Leica epifluorescence optical microscope (40× or 63× immersion lens). The images were taken with a digital Nikon Coolpix camera with maximum zoom and a 0.63× adapter. A more detailed analysis was performed with a confocal Bio-rad MRC 600 microscope (BIO-RAD Microscience Ltd., Hemel Hempstead, England), provided with an inverse optical microscope and an ×100 immersion lens. The bacteria were visualized by their fluorescence after excitation with a krypton/argon laser. Several sections of 0.1-0.2 μm bacteria were made.

I.8.b) Evaluation of the Penetration of the Conjugates in the Bacterium at +4° C.

The method described above (1.8.a) was modified in the following way. The bacteria immobilized on a poly-L-Lysine slide and rinsed 3 times with the NAPB buffer were incubated for 24 hours at +4° C. before adding DPV fluorescent, conjugates preincubated at +4° C. All the following stages were done at +4° C. with cold solutions.

I.9) Immunomarking of the External Membrane of the Bacteria: Indirect Immunofluorescence.

The bacteria immobilized on a poly-L-Lysine slide were rinsed 3 times with NAPB buffer and incubated 30 minutes at laboratory temperature with a 0.05% NAPB/SAB (Serum Albumin Bovine) solution. The bacteria were incubated 30 mins. at laboratory temperature with mouse antiendotoxin monoclonal antibody (Biovalley Cat #C55157; batch #212529) diluted in NAPB/SAB 0.05%, and washed several times with 0.05% NAPB/SAB, and then incubated 30 minutes at laboratory temperature, away from light, with a second antibody: rabbit polyclonal antibody anti-mouse, tetramethylrhodamine (TRITC) (Jackson ImmunoResearch Cat #315-026-003, batch #47511) or fluoresceine (FITC) ((Jackson ImmunoResearch Cat #715-095-150, batch #51038) conjugated. After several washings with NAPB-buffer, a drop of 50% PBS/Glycerol was deposited on the slide and covered by a cover glass. After sealing the cover glass on the slide, the fluorescence of the bacteria was observed in a confocal microscope, as described above (Section 1.8.a).

I.10) Evaluation of the Antibacterial Activity of the Conjugates.

The minimum inhibitory concentrations (MIC) were determined by the microdilution method in a liquid medium (NC-CLS M7A5) for the set of bacterial species in 96-well polystyrene plates.

An isolated colony of the bacterium *E. coli* ATCC 25922 or *P. Aeruginosa* ATCC 27853 was placed in suspension in 3 to 5 ml of Mueller-10 Hinton (MH) culture medium and incubated at 37° C. for one night, while stirring. From this night culture, a culture in an exponential growth phase of the strain was made; the MH medium was is seeded at a 2 percent ratio with the night culture and incubated for 2 hours at 37° C., while stirring. The bacterial concentration was adjusted to $1 \times 10^6$ cfu/ml (colony-forming units) in the MH medium.

50 µl of bacterial inoculum was distributed per well containing an equal volume of the conjugate solution diluted half and half in the appropriate culture medium (0 to 1 µM). The cultures were incubated at 37° C. in ambient air for 16 to 20 hours.

The CMI expressed in µM is the first concentration not exhibiting bacterial growth.

II—Results.

II.1) Internalization of DPV-Bodipy Conjugates in the Gram-Negative bacterium.

II.1.a) Qualitative Evaluation of the Internalization of DPV-Bodipy Conjugates.

Qualitative Evaluation of the *E. coli* Bacterium.

Figure 3:
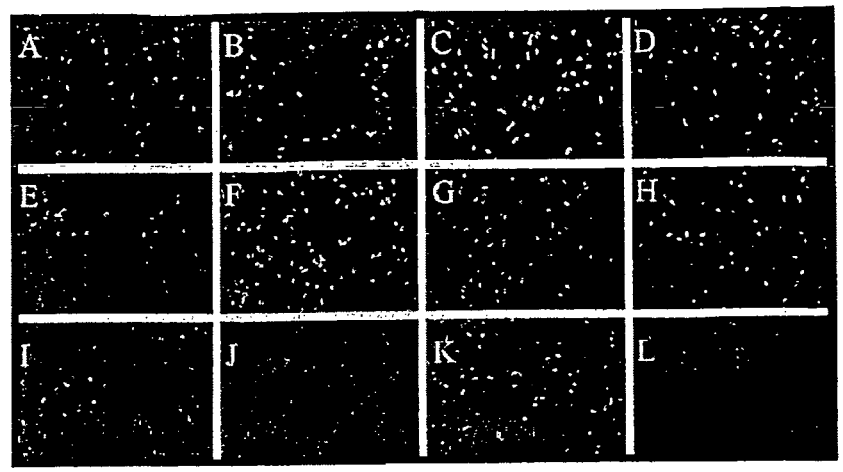
FIG. 3 represents the internalization of the DVP-Bodipy conjugates in *E.coli*.

FIG. 3 shows the internalization of DPV-Bodipy conjugates in *E. coli*.

The immobilized bacteria on a poly-L-Lysine slide were incubated with 1 µM of DPV-Bodipy conjugate for 30 minutes at 37° C. The microscopy images (epifluorescence optical microscope, ×63 immersion lens) shows the penetration of DPV-Bodipy conjugate in the living bacteria. A: DPV3, B: DPV3.10; C: DPV6; D: DPV7; E: DPV7b; F: DPV15; G: 10 DPV15b; H: DPV1047; I: DPV11; J: DPV12; K: DPV1121; L: DPV19.

The *E. coli* bacteria were incubated for 30 minutes at 37° C. with 1 µM of DPV-Bodipy conjugate, as described in paragraph I.8.a. The internalization of fluorescent DPV-Bodipy conjugates in the non-fixed bacteria was visualized under an epifluorescence microscope. No fluorescence was detected with Cys-Bodipy conjugate control. As shown in FIG. 3, several DPV-Bodipy conjugates passed the bacterial membranes of the *E. coli* bacterium to accumulate in the bacterial cytoplasm. The DPV3.10 peptides (FIG. 3B), DPV3 (FIG. 3A), DPV6 (FIG. 3C) and DPV15 peptides (FIG. 3F) were highly penetrating and internalizing of hydrophobic molecules. With the DPV11 and DPV12 peptides (FIGS. 3I and 3J), heterogeneous fluorescence levels in one single bacterial population was obtained. The internalization properties of these peptides were weaker. The DPV19 peptide did not penetrate into the bacteria. (FIG. 3L).

An identical internalization profile of the DPV-Bodipy conjugates was observed after fixation of the bacteria.

Figure 4:
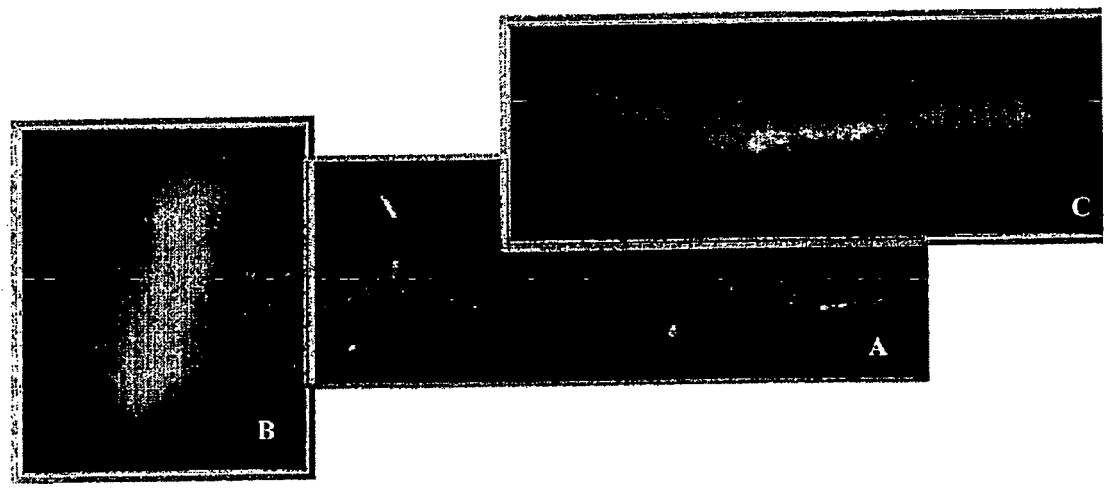
FIG. 4 represents the immunomarking of the external membrane following internalization of the DPV3-Bodipy conjugate.

FIG. 4 represents the immunomarking of the external membrane after internalization of the DPV3-bodipy conjugate.

The *E. coli* bacteria immobilized on a poly-L-Lysine slide were incubated with 3 µM of DPV3-Bodipy conjugate at 37° C. for 30 minutes. After internalization, the external membrane of the living bacteria was detected by immunomarking using mouse antiendotoxin monoclonal antibody and rabbit polyclonal antibody anti-Ig G of mouse coupled to TRITC.

The localization of the DPV3-Bodipy conjugate (green fluorescence) and the immunomarking of the external membrane (red fluorescence) was observed with a confocal microscope. A: Original image size; B and D: Two enlargements of the bacteria of Image A.

In order to confirm the localization of DPV-Bodipy conjugates In the bacterial cytoplasm, the *E. coli* bacteria were incubated with 3 µM of DPV3-Bodipy conjugate, as described in Paragraph 1.8, and the external membrane of the living bacteria was visualized by specific immunomarking, as described in Paragraph I 9. Endotoxin is a specific constituent of the external membrane of Gram-negative bacteria. The fluorescence of bacteria was visualized in a confocal microscope (FIG. 4). The Bodipy internalization was visualized by green fluorescence and the external membrane was identified by red fluorescence. The analysis of these images clearly showed that DPV3 peptide passes through the external and internal membranes of the Gram-negative *E. coli* bacterium and allows the accumulation of Bodipy in the bacterial cytoplasm.

Qualitative Evaluation in the *P. aeruginosa* Bacterium.

Figure 5:
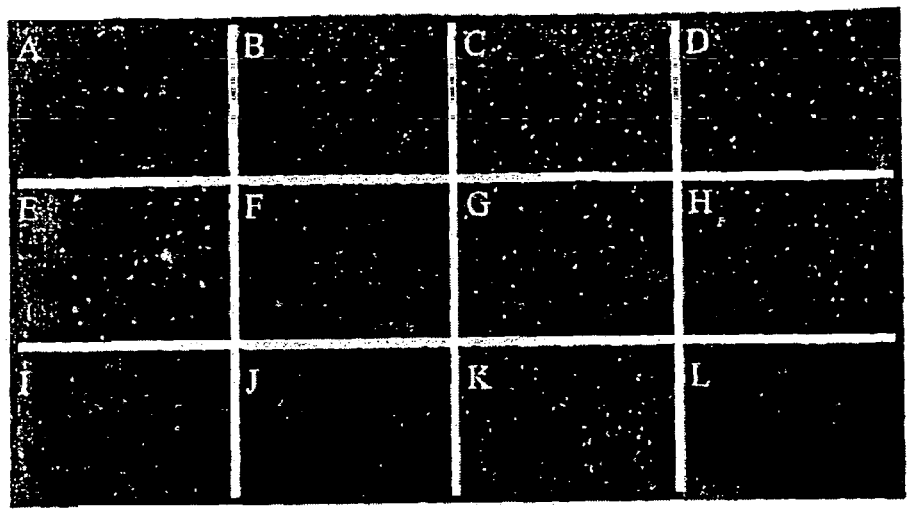
FIG. 5 represents the internalization of the DPV-Bodipy conjugates in *P. aeruginosa*.

FIG. 5 represents the internalization of DPV-Bodipy conjugates in *P. aeruginosa*.

The bacteria immobilized on a slide were incubated with 1 µM of DPV-Bodipy conjugate for 30 minutes at 37° C. The microscopy images, (epifluorescence optical microscope, × 63 immersion lens) showed the penetration of DPV-Bodipy conjugate in the living bacteria. A: DPV3, B: DPV3.10; C: DPV6; D: DPV7; E: DPV7b; F: DPV15; G: DPV15b; H: DPV1047; I: 10 DPV11; J: DPV12; K: DPV1121; L: DPV19.

Figure 6:
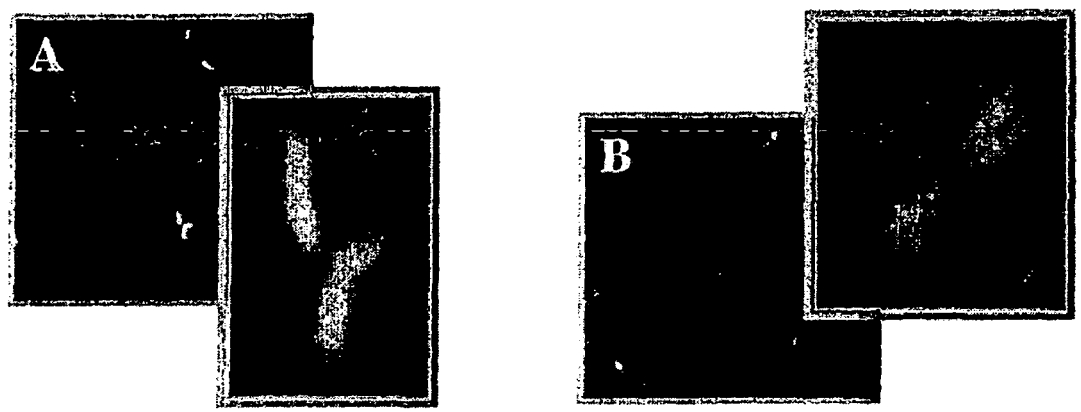
FIG. 6 provides images of confocal microscopy of *P. aeruginosa*.

FIG. 6 provides confocal microscopy images of *P. aeruginosa*.

The bacteria were immobilized on a poly-L-Lysine slide and incubated with 3 µM of DPV3-Bodipy conjugate (A) or DPV7-Bodipy conjugate (B) at 37° C. for 30 mins., and subsequently fixed on the slide. The bacteria were observed in a confocal microscope. An enlargement of the original image of the bacteria was presented.

A similar qualitative evaluation was done on *P. aeruginosa*. FIG. 5 shows the internalization of the conjugates in the bacteria after 30 minutes of incubation. The properties of the DPV internalization were identical to those observed for *E. coli*, except for the DPV7b and DPV6 peptides that appear to be more internalizing in *P. aeruginosa*. The observation in the confocal microscope (FIG. 6) of bacteria incubated with the DPV3 or DPV7b peptides reveals that these peptides are able to pass through the external membrane and allow the accumulation of Bodipy in bacterial cytoplasm.

II.1.b) Classification of DPVs.

As shown in FIGS. 3 and 5, the level of accumulation of DPV-Bodipy conjugates in bacterial cytoplasm varies according to the DPV and the bacterial strain. Generally, the internalization of DPV is almost identical for the two bacterial strains that were studied. The DPV peptides may be divided into three major groups:

DPV3, DPV3.10: elevated internalization
DPV6, DPV7, DPV7b, DPV15: medium internalization
DPV15b, DPV1047, DPV1121: weak internalization The DPV3.10, DPV3, DPV6, DPV7 and DPV7b peptides have been described previously as cytoplasmic localization peptides in the eukaryotic cells (international PCT patent application published under No. WO 01/64738), when they are chemically coupled to the peroxydase protein or IgG. In contrast, the DPV15, DPV15b, DPV1047 and DPV1121 peptides were described as nuclear localization peptides. It is important to note that the internalization level of the "nuclear" DPV is weaker than it is for "cytoplasmic" DPV. The peptides with cytoplasmic tropism are more internalizing in the bacterium.

As shown in Table 1 below, the DPV19, DPV11 and DPV12 peptides do not have any internalization properties in the eukaryotic cell. The same property was observed with the prokaryotic cells, as [with] the Gram-negative bacteria.

Table 1: Qualitative Evaluation of the Internalization of DPV-Bodipy Conjugates in the Gram-Negative Bacterium.

TABLE 1

|              | E. coli | P. aeruginosa |
|--------------|---------|---------------|
| DPV3~Bodipy    | +++     | +++           |
| DPV3.10~Bodipy | ++++    | ++++          |
| DPV6~Bodipy    | ++      | +++           |
| DPV7~Bodipy    | ++      | ++            |
| DPV7b~Bodipy   | +       | +++           |
| DPV15~Bodipy   | ++      | ++            |
| DPV15b~Bodipy  | +       | +             |
| DPV1047~Bodipy | +       | +             |
| DPV1121~Bodipy | +       | +             |
| DPV19~Bodipy   | −       | −             |
| DPV11~Bodipy   | +/−     | +/−           |
| DPV12~Bodipy   | −       | −             |

II.1.c) Study of the Effect of poly-L-Lysine (Bacterial Support) on Internalization.

In order to confirm the preceding results and evaluate a potential interference of poly-L-Lysine with the internalization of conjugates, the E. coli bacteria were incubated with the DPV-Bodipy conjugates for 30 minutes at 37° C., and then extensively washed with the NAPB buffer before being immobilized and either fixed or not on a poly-L-Lysine slide. The localization of conjugates was visualized in an epifluorescence or confocal optical microscope. The internalization properties of the various DPVs did not vary from the previously obtained results. Poly-L-Lysine has no effect on the capacity of DPV to pass through the bacterial membranes and penetrate into the bacterium.

II.1.d) Influence of the Temperature on the Internalization Level.

In order to explain the previously observed internalization mechanism, the capacity of DPV to internalize at +4° C. was analyzed. The E. coli bacteria in the exponential phase of growth were immobilized on a poly-L-Lysine slide, and then incubated for 24 hours at +4° C. in order to eliminate the energetic metabolism of the bacterium. The bacteria were subsequently incubated with 3 µM of DPV7-Bodipy or Cyst-Bodipy (control) for 30 minutes at +4° C., as described in Paragraph I.8.b), and washed extensively before visualization in an epifluorescence and confocal optical microscope. In order to compare the internalization levels at 37° C. and +4° C., the same experiment was conducted at 37° C., as described in Paragraph I.8.a.

The internalization level of DPV7 in the bacterium was the same, regardless of the temperature of the experiment. Thus, it appears that the internalization of the DPV7-Bodipy conjugate in E. coli is not an energy-dependent mechanism. The phenomenon is likely a passive translocation across bacterial membranes.

II.2) Internalization of DPV3-TMR Conjugate in E. coli.

It was shown that certain DPV peptides may pass through the external membrane of Gram-negative bacteria and penetrate into the bacterium to internalize a hydrophobic compound, such as Bodipy, that is normally excluded by this external membrane.

In order to validate the previously obtained results and exclude any influence of Bodipy fluorescent tracer on the internalization, identical experiments were conducted with a second hydrophobic fluorescent tracer, i.e., TMR. TMR differs from Bodipy in its physiochemical properties, such as structure or the presence of a positive charge (FIG. 2).

Figure 7:
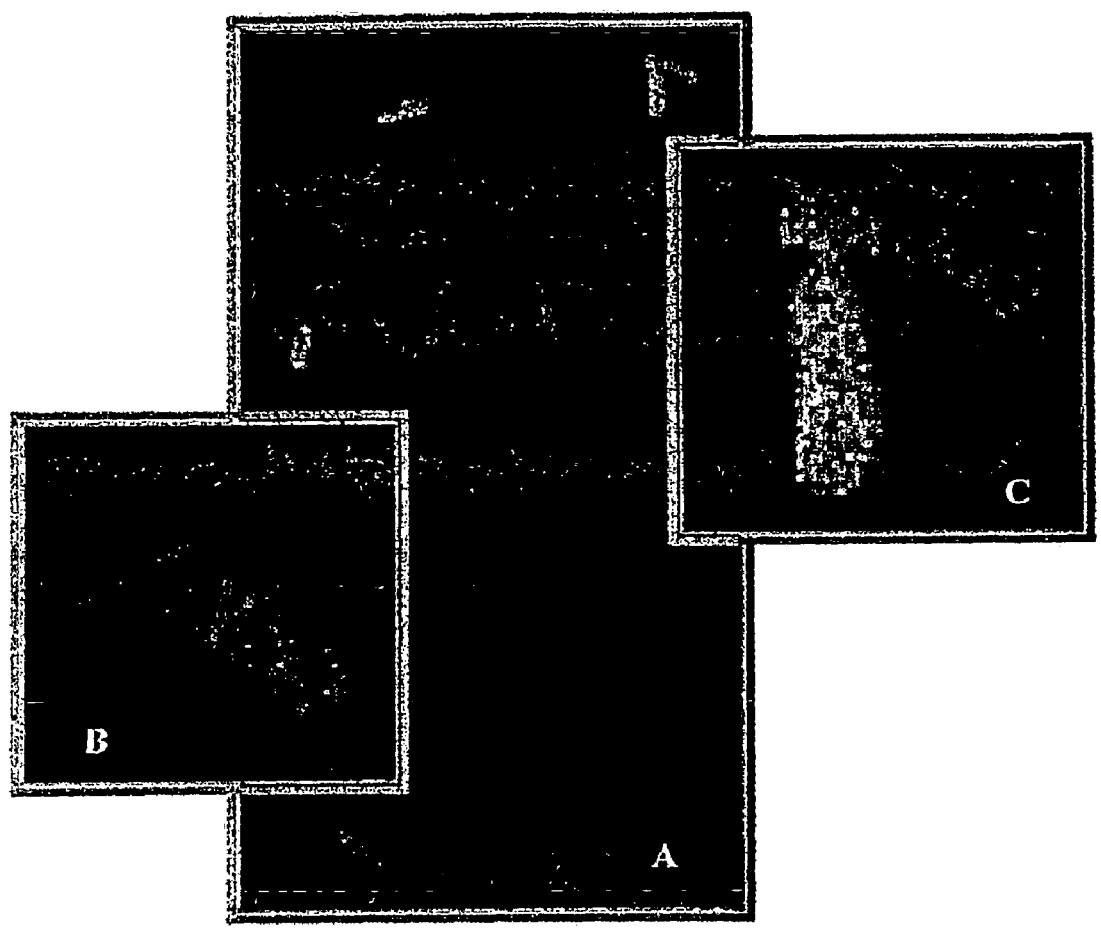
FIG. 7 represents internalization of the DPV3-TMR conjugate in *E. coli*.

FIG. 7 represents the internalization of the DPV3-TMR conjugate in E. coli.

The E. coli bacteria were immobilized on a poly-L-Lysine slide and incubated with 1 µM of DPV3-TMR conjugate at 37° C. for 30 mins. After internalization, the external membrane of the living bacteria was detected by immunomarking using mouse antiendotoxin monoclonal antibody and rabbit polyclonal antibody anti-Ig G of mouse coupled to FITC. The localization of the DPV3-TMR conjugate (red fluorescence) and the immunomarking of the external membrane (green fluorescence) were observed in a confocal microscope. A: Original size of the image; B and D: Two enlargements of the bacteria in Image A.

The internalization of the DPV3 TMR conjugate was evaluated on E. coli bacteria immobilized on a poly-L-Lysine slide or in suspension. The bacteria were incubated with 1 µM of DPV3-TMR conjugate or the Cyst-TMR control for 30 minutes at 37° C., and then either fixed or not on the slide before visualization in an epifluorescence optical microscope. Regardless of which internalization protocol was used, fluorescence was not detected with the control conjugate, whereas DPV3-TMR was visualized by red fluorescence of the bacterium.

In order to confirm the internalization of the DPV3-TMR conjugate, the bacteria were immobilized on a poly-L-Lysine slide and incubated with 1 µM of conjugate at 37° C. for 30 minutes. Immunomarking of the external membrane was done by using mouse monoclonal antibody antiendotoxin and rabbit polyclonal antibody anti-IgG of mouse coupled to FITC. The localization of the DPV3-TMR conjugate was observed in a confocal microscope (FIG. 7). The DPV3-TMR conjugate passes through the external membrane, penetrates into the bacterium and accumulates in the cytoplasm. This result was identical to those obtained with the Bodipy fluorescent tracer.

II.3) Anti-Bacterial Activity of the DPV Conjugates.

In order to determine that the internalization of the DPV conjugates does not induce death of the bacteria, the 12 DPV-Bodipy conjugates and the DPV3-TMR conjugate were tested for their anti-bacterial activity, as described in Paragraph 1.10) None of the conjugates tested showed any anti-bacterial activity on E. coli at the concentrations used in the internalization experiments. This experiment showed that the internalization of the conjugates has no effect on bacterial viability. The internalization mechanism in the bacterium is non-toxic.

III—Internalization of a DPV-Antibiotic Conjugate (Example: DPV-Erythromycin)

III.1) Synthesis of a DPV-Antibiotic Conjugate

III.1.a) Activation of the Erythromycin by a Heterobifunctional Cross Linker

A solution of maleimidocaproic acid (MIC) (2.8 equivalents) and dicyclohexylcarbodiimide (DCC) (2.8 equivalents) in the dimethylformamide (DMF) was stirred overnight at 0° C. under argon, and away from light. The formed precipitate (dicyclohexylurea) was eliminated by filtration, washed with DMF, and subsequently refiltrated. An antibiotic (1.0 equivalent) and pyridine (5.0; equivalents) solution in the DMF was stirred until completely dissolved. The filtrate obtained above was added to this solution; the mixture was stirred for one hour at ambient temperature.

The solution was resumed in distilled water, washed four times with dichloromethane (DCM). The obtained organic phases were collected and washed successively with hydrochloric acid (HCl) 0.1 N, two times with disodium carbonate ($Na_2CO_3$), and three times with water ($H_2O$). After drying on magnesium sulphate (MgSO4) and concentration, the washed reagent crude was purified by flash chromatography on silica (eluent $CH_2C_{12}$/MeOH).

III.1.b) Coupling of Activated Erythromycin with a Penetrating DPV Peptide.

A penetrating peptide (1.0 equivalent) in a buffer solution of sodium phosphate ($NaH_2PO_4/Na_2HPO_4$) of 10 mM and pH 7.1 was stirred for five minutes at ambient temperature under argon, and away from light. The activated antibiotic (1.5 to 2.0 equivalents), dissolved in the minimum of DMF, was then added. The solution was stirred until complete transformation of the peptide (followed by HPLC). Distilled water was subsequently added, and the aqueous phase extracted three times with the same volume of dichloromethane in order to eliminate the excess of activated antibiotic. The aqueous phase was then freeze-dried for preparative HPLC. The penetrating antibiotic peptide was therefore isolated with yields between 45 and 100% and purities above 90%.

III.2) Evaluation of the Antimicrobial Activity of the DPV-Erythromycin Conjugates.

The minimum inhibitory concentrations (CMI) of conjugates were determined with the microdilution method in a liquid medium according to the NCCLS-M7A5 (National Committee for Clinical Laboratory Standards—Document M7A5) standards for the set of bacterial species in a 96-well polystyrene plate.

Protocol:

A column isolated by a bacterium (e.g., *E. coli* or *P. aeruginosa*) was placed in suspension in 3 to 5 ml of Mueller-Hinton (MH) culture medium and incubated at 37° C. for one night, while stirring. From this night culture, a culture in exponential growth phase of the strain is realized; The MH medium was seeded at a 2 percent ratio with the night culture and incubated for 2 hours at 37° C., while stirring. The bacterial concentration was adjusted to at 1×10 s cfu/ml (colony-forming units) in the MH medium.

50 μl of bacterial inoculum was distributed by wells containing a volume equal to the conjugate solution diluted half and half in a proper culture medium (512 at 0.5 μg/ml). The cultures were incubated at 37° C. in ambient air for 16 to 20 hours.

CMI expressed in μg/ml (International Units) is the first concentration that did not present bacterial growth. Determining the minimum concentration of bactericide (MCB) was done after reading the CMI plates. The CMB is the lowest concentration of conjugate inhibiting all bacterial growth on the subculture agar (<0.1% of survivors).

IV—Evaluation of the Antibacterial Activity of the Association of a DVP Peptide and Erythromycin A by the So-Called Chessboard Method.

IV-1) Materials and Methods

Selected peptides: DPV3 and DPV3.10

Antibacterial compound: Erythromycin (Sigma E0774)

Bacterial strains: *E. coli* ATCC 25922 and *P. aeruginosa* ATCC 27853.

This method was done in 96-well polystyrene microplates in a Mueller-Hinton (MH) culture medium and consisted in exposing a bacterial suspension to different concentrations of DPV peptide and erythromycin, used alone or in association.

The final selected concentrations of erythromycin and peptide were spaced part 256 to 4 μg/ml and 256 to 2 μ/ml, respectively. The dilution ranges were prepared according to a geometric progression of ration 2.

25 μl of the product solutions in MH medium with a concentration four times higher than the desired final concentration or 25 μl of the MH medium (for the lines 0), were distributed in the wells according to the chart below (Table 2), in order to obtain a final volume of 50 μl per well:

Table 2: Distribution of Product Solutions in MH Medium (the Wells Marked X Were Not Used)

TABLE 2

| | Final concentration of DPV peptide (μg/ml) | | | | | | | | |
|---|---|---|---|---|---|---|---|---|---|
| | 0 | 256 | 128 | 64 | 32 | 16 | 8 | 4 | 2 |
| [Symbol] 0 | | | | | | | | X | X |
| 256 | | | | | | | | X | X |
| 128 | | | | | | | | X | X |
| 64 | | | | | | | | X | X |
| 32 | | | | | | | | X | X |
| 16 | | | | | | | | X | X |
| 8 | | | | | | | | X | X |
| 4 | | | | | | | | X | MH |

An isolated colony of the bacterium *E. coli* ATCC 25922 or *P. aeruginosa* ATCC 27853 was placed in suspension in 3 to 5 ml of the MH culture medium and incubated at 37° C. for one night, while stirring. From this night culture, a culture in exponential growth phase of the strain was made; the MH medium was seeded at 1/50 é with the night culture and incubated for two hours at 37° C., while stirring. The bacterial concentration was adjusted to 5×105-10 s cfu/ml (colony-forming units) in the MH medium. 50 μl of bacterial inoculum was distributed by wells containing an equal volume of the peptide and/or erythromycin solution. The CMI of the peptide and erythromycin was determined, as the weakest concentration causing the absence of bacteria (absence of turbidity) after 18 hours culture in a drying chamber at 37° C. The CMI was expressed in μg/ml (mg/1). For each well line, the first wells containing the DPV peptide and erythromycin association not presenting any visible growth were noted in order to calculate for each line the fraction index of the inhibitory concentration (FIC) using the following formula:

$$FIC = (CMI \text{ of the peptide with erythromycin}/CMI \text{ of the peptide alone}) + (CMI \text{ of the erythromycin with the peptide}/CMI \text{ of the erythromycin alone})$$

This index makes it possible to quantify the association. An index below or equal to 0.5 indicates a synergy, an index above 2, an antagonism. An addition effect is indicated by an FIC between 0.5 and 1, and an indifference effect, by an FIC, whose values are between 1 and 2.

IV.2) Results

The Gram-negative bacteria such as *E. coli* and *P. aeruginosa* are resistant to antibiotics of the macrolides family due to the non-penetration of these antibiotics across the external membrane of the bacterium. In order to evaluate the internalizing properties of the DPV peptides that were previously identified and their capacity to facilitate penetration of an antibiotic of the macrolides family, the antibacterial activity of the erythromycin on the *E. coli* and *P. aeruginosa* bacteria was evaluated in association with the DPV3 or DPV3.10 peptide according to the so-called chessboard method.

The synergy effect of the association of the DPV3 and 3.10 peptides with erythromycin is shown in Tables 3 and 4. In the presence of DPV3, a synergy effect with the erythromycin was observed only on *E. coli* showing that this peptide allows the entrance of erythromycin in *E coli*. The DPV3.10 association with erythromycin is synergetic on the two bacterial strains. The DPV3.10 peptide at the non-toxic concentration of 32 μg/ml allows the penetration (internalization) of erythromycin.

Table 3: Determination of CMIs and FICs of erythromycin in association with DPV3

TABLE 3

| Bacteria | CMI (μg/ml) | | | Index FIC | Synergy |
|---|---|---|---|---|---|
| | Erythromycin alone | DPV3 alone | Erythromycin associated with DPV3* | | |
| *E. coli* | 256 | 256 | 64 (64) | 0.5 | Yes |
| *P. aeruginosa* | 256 | 256 | 64 (64) | 0.75 | No |
| | | | 4 (128) | 0.52 | No |

*The values within parentheses are the concentrations (μg/ml) of added DPV3

Table 4: Determination of the CMIs and FICs of erythromycin in the presence of DPV3.10 peptide.

TABLE 4

| Bacteria | CMI (μg/ml) | | | FIC index | Synergy |
|---|---|---|---|---|---|
| | Erythromycin alone | DPV3 alone | romycin associated with PV3* | | |
| *E. coli* | 256 | 128 | 64 (32) | 0.5 | Yes |
| *P. aeruginosa* | 256 | | 32) | 0.375 | |

*the values within parentheses are the concentrations (μg/ml) of added DPV3.10.

The invention claimed is:

1. An antibacterial composition for the control of Gram-negative bacteria comprising an amount of one or more identical or different peptide and one or more identical or different antibacterial compound either in the form of a mixture or in the form of a product in which said one or more peptide is directly covalently bound to said one or more antibacterial compound and wherein said one or more peptide is selected from the group consisting of SEQ ID NO:2, SEQ ID NO:5, SEQ ID NO:6, and SEQ ID NO:7.

2. An antibacterial composition for the control of Gram-negative bacteria comprising one or more identical peptide and one or more identical or different antibacterial compound, either in the form of a mixture or in the form of a product in which said one or more peptide is directly covalently bound to said one or more antibacterial compound, and wherein said peptide consists of SEQ ID NO: 1.

3. A composition for the control of Gram-negative bacteria comprising an amount of one or more identical or different peptide and one or more identical or different antibacterial compound, which is selected from the group consisting of a macrolide, a ketolide and a combination of a macrolide and ketolide, either in the form of a mixture or in the form of a product in which said one or more peptide is directly covalently bound to said one or more antibacterial compound, and wherein said one or more peptide is selected from the group consisting of SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO:11.

* * * * *